United States Patent [19]

Imamichi et al.

[11] Patent Number: 4,786,163

[45] Date of Patent: Nov. 22, 1988

[54] AUTO-KERATOMETER

[75] Inventors: Masatsugu Imamichi; Takashi Nishiguchi, both of Kyoto, Japan

[73] Assignee: Sun Contact Lens Co. Ltd., Japan

[21] Appl. No.: 944,741

[22] Filed: Dec. 19, 1986

[30] Foreign Application Priority Data

Jul. 22, 1986 [JP] Japan .................... 61-113110[U]

[51] Int. Cl.$^4$ ............................................. A61B 3/10
[52] U.S. Cl. ................................... 351/212; 351/211
[58] Field of Search ............... 351/212, 211, 247, 221, 351/214

[56] References Cited

U.S. PATENT DOCUMENTS

| 4,046,463 | 9/1977 | LaRussa et al. | 351/212 |
| 4,490,022 | 12/1984 | Reynolds | 351/212 |
| 4,660,947 | 4/1987 | Amoils | 351/212 |

OTHER PUBLICATIONS

Brochure published in the United Kingdom by Keeler Limited entitled "Keeler Amoils Surgical Astigmometer".

Primary Examiner—Rodney B. Bovernick
Assistant Examiner—P. M. Dzierzynski
Attorney, Agent, or Firm—Kirschstein, Kirschstein, Ottinger & Israel

[57] ABSTRACT

An auto-keratometer attached to an operating microscope to measure the refraction and astigmatic condition of the cornea comprises a cornea irradiating light source section disposed below the operating microscope, and switching means for selectively switching the light source section between an irradiating position on the optical axis and a retracted position. When it is desired to measure the corneal condition, the light source section is set at the irradiating position below the operating microscope, so that the light from the light source section reflected by the cornea travels through a beam splitter and is detected by a detector, whereby the refraction or astigmatic condition of the cornea is measured. If the light source section is found interfering with the operation, the light source section is set at the retracted position by rotating it through 180 degrees, whereby the working region below the microscope is widened to facilitate the operator's surgical operation on the cornea.

7 Claims, 2 Drawing Sheets

AUTO-KERATOMETER

BACKGROUND OF THE INVENTION

The present invention relates to an auto-keratometer for automatically measuring an abnormal curving or astigmatic condition of the cornea, and more particularly it relates to improvements in a means for attaching a light source section therefor.

Generally, in operations on the cornea, such as for cataract and corneal transplantation, to provide good eyesight after operation it is necessary to accurately control the corneal shape while measuring the corneal refraction or corneal astigmatic condition making allowance for a possible change in the corneal shape.

Thus, it has been common practice to make automatic measurements of the corneal condition by installing a light source section having a built-in fluorescent lamp and stroboscopic lamp under an existing operating microscope, causing the light from said light source section to strike on the patient's eye, adjusting the vertical position of the microscope while observing the reflected image of the cornea with the eyepiece through the objective lens of the microscope and a beam splitter, and, upon completion of the alignment, indicating the result of the measurement on a display or printing it out.

In the microscope described above, however, the vertical working distance below said microscope is as short as about 175 mm, accounting for the fact that installing a measuring light source such as a ring light source below the microscope has entailed the danger of causing trouble to surgical operation. For this reason, there has been a desire for maximizing the working region below the microscope and above the cornea.

In the case of an operation on the cornea, it has been necessary to install an assistant microscope to allow an assistant to observe the corneal condition in conjunction with the operator. However, since the space below the microscope is limited, it has been sometimes impossible to attach the assistant microscope to the operating microscope. Even if the assistant microscope can be attached thereto, the light source for the auto-keratometer forms an obstacle which limits the attachment of the assistant microscope to a position located laterally of the microscope. As a result, the viewing angle of the objective lens of the assistant microscope relative to the cornea is increased, making it impossible to obtain the same field of vision as that for the operator, thus posing a problem in operation.

SUMMARY OF THE INVENTION

The present invention, which has been accomplished with the above in mind, provides an auto-keratometer which is adapted to be attached to an operating microscope having an eyepiece in the upper region thereof and an objective lens in the lower region and which is designed to measure the corneal refraction or corneal astigmatic condition by detecting the light from a light source reflected by the cornea through the intermediary of said objective lens and a beam splitter, said auto-keratometer being characterized by the provision of a cornea irradiating light source section attached to the lower portion of said operating microscope, and switching means for selectively turning said light source section for switching between an irradiating position on the optical axis and a retracted position.

With the above arrangement thus made, according to the present invention, the corneal condition is measured during an ophthalmic operation by the auto-keratometer by setting the light source section at the irradiating position on the optical axis below the operating microscope to detect the light from the light source section reflected by the cornea using a suitable detector, whereby the corneal refraction or astigmatic condition is measured.

When the light source section interferes with the operation during incision of the patient's cornea or suturation, the light source is turned through about 180 degrees for setting at the retracted position, whereby the working region below the microscope is widened to facilitate the operation on the cornea.

In that case, since said light source section is turnably attached to the operating microscope, the viewing angle relative to the patient's cornea can be kept small by positioning the assistant microscope between the light source and the lower end surface of the operating microscope even if the assistant microscope is attached to the operating microscope; thus, substantially the same field of vision as that for the operator can be obtained with the assistant microscope.

OBJECTS OF THE INVENTION

In view of the above, the invention is intended to improve the method of attaching the light source section of the auto-keratometer such that even when the auto-keratometer is installed on the operating microscope, this causes no interference with the operator's surgical operation while making it possible to attach an assistant microscope which has substantially the same field of vision as that for the operator.

BRIEF DESCRIPTION OF THE DRAWINGS

The drawings illustrate an embodiment of the invention.

DETAILED DESCRIPTION OF THE PREFERRED EMBODIMENT

An embodiment of the invention will now be described with reference to the drawings.

Figure 1:
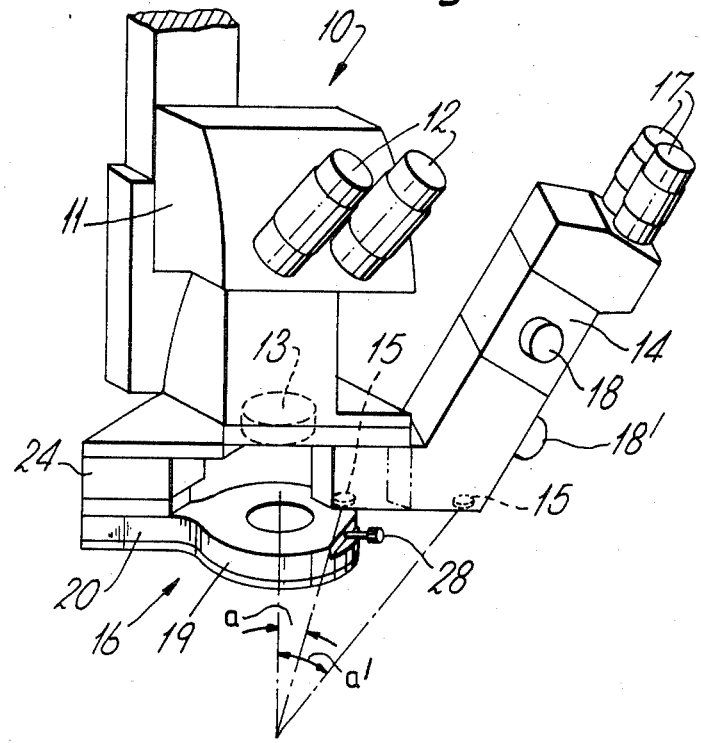
FIG. 1 is a perspective view showing the entire arrangement of an operating microscope having an auto-keratometer applied thereto.

FIG. 1 shows the entire arrangement of an operating microscope 10 having an auto-keratometer according to the present invention applied thereto. In this figure, the numeral 11 denotes the body of the operating microscope 10. An eyepiece 10 is disposed in the upper region of said body 11 and an objective lens 13 in the lower region.

Disposed laterally of said operating microscope 10 is an assistant microscope 14 whose objective lens 15 is adapted to be positioned between said operating microscope 10 and a rotatable member 16 to be later described. In addition, the numeral 17 denotes the eyepiece of said assistant microscope; 18 denotes a magnification adjusting screw; and 18' denotes a focus adjusting screw.

Figure 2:
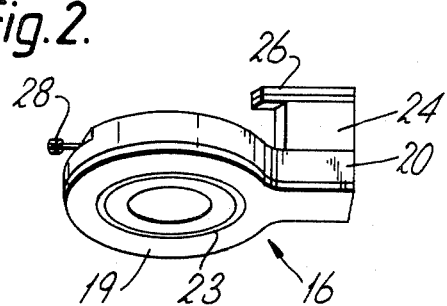
FIGS. 2 and 3 are a perspective view and a side view of a rotatable member respectively.
Figure 3:
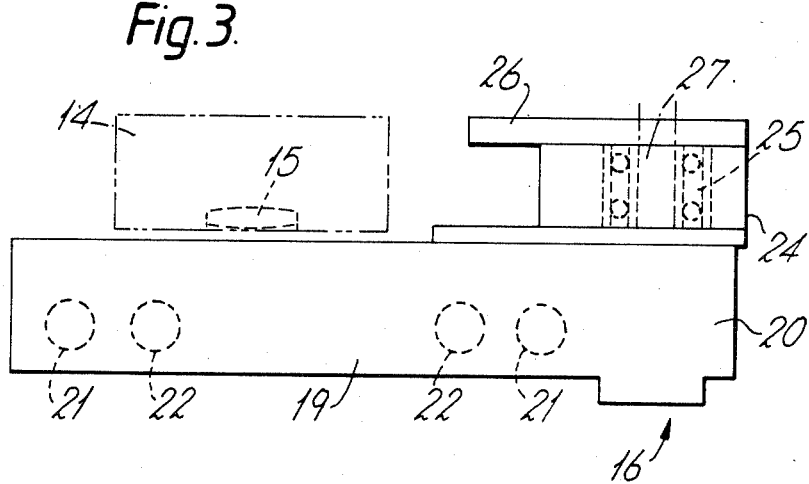

The rotatable member 16 is disposed in the lower region of the body 11. The rotatable member 16, as shown in FIGS. 2 and 3, comprises an annular, cornea irradiating light source 19 and a base end section 20 outwardly extending from a portion of said light source section 19. Housed in said light source section 19 are a fluorescent lamp 21 serving as a light source for examining the cornea, and a stroboscopic lamp 22 for measuring the corneal shape, the arrangement being such that the light from said fluorescent lamp 21 or stroboscopic lamp 22 is directed downward through a projection index 23 made of transparent acrylic resin, having a circular slit and disposed on the lower surface of the light source section 19. A connecting member 24 serving as switching means disposed on said base end section 20 has a bearing 25 built therein to support a support shaft 27 which extends downward from an attaching table 26 fixed to the lower end of said microscope 10. Thus, said rotatable member 16 is mounted for rotation on said support shaft 27 and is adapted to selectively switch said light source section 19 between an irradiating position on the optical axis and a retracted position. In addition, the numeral 28 denotes a rotation adjusting knob attached to the front end of said rotatable member 16.

With this arrangement, when it is desired to measure the corneal shape in the central narrow region of the cornea, the rotatable member 16 is set at the upper limit position (the solid line position shown in FIG. 4), whereupon the light from the light source passes through said projection index 23 to strike on the cornea A of a patient. The light reflected by the cornea A passes through the objective lens 13 and is partly reflected by a beam splitter 29 to travel through relay lenses 30 to two half mirrors 31 which divide the light into three parts which then focus on the light receiving surfaces of three CCD elements 32 serving as detectors, these parts of light thus received being then processed for arithmetic operation by a CPU, whereby the corneal refraction or corneal astigmatic condition can be measured.

Figure 4:
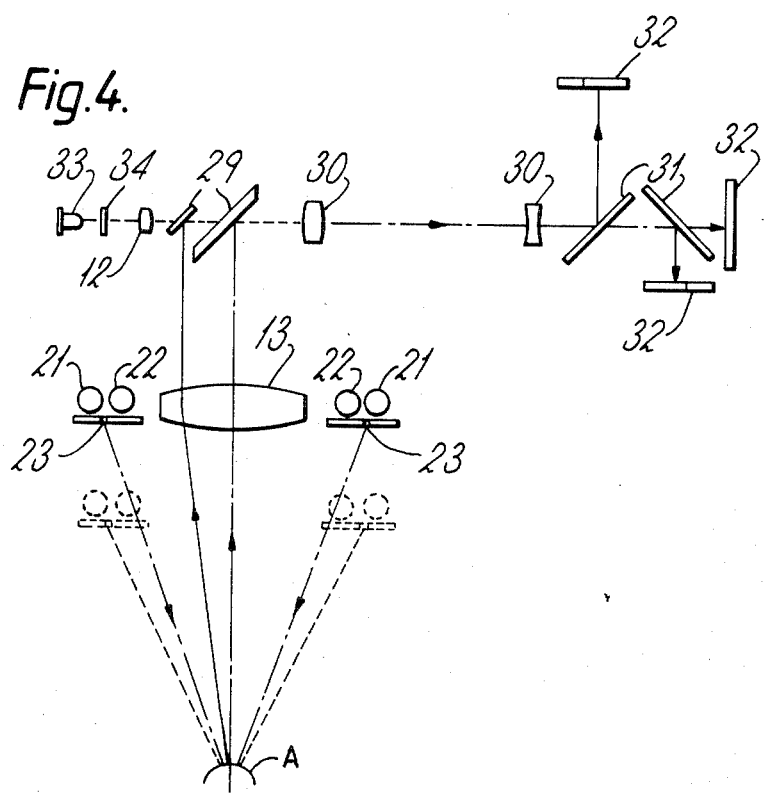
FIG. 4 is a view showing the optical principle of the auto-keratometer.

On the other hand, when it is desired to measure the corneal shape in the wider region of the cornea, said rotatable member 16 is set at the lower limit position (the broken line position in FIG. 4), whereupon the light from the light source travels through said projection index 23 in the directions of broken arrows in FIG. 4 to fall on the patient's cornea, whereafter the light travels the same path as that described above, focusing on the light receiving surfaces of the CCD elements 32, so that the corneal refraction or corneal astigmatic condition can be measured.

In addition, the numeral 33 denotes a light-emitting diode, and 34 denotes an alignment index for adjusting the vertical position of said operating microscope 10.

Thus, according to the above embodiment, since said rotatable member 16 is rotatably attached to said operating microscope 10, it can be rotated, when necessary, during ophthalmic operation to a position where it does not interfere with the operation, thereby widening the working region for surgical operation above the cornea of the patient. Thus, even when the operating microscope 10 is equipped with an auto-keratometer and the rotatable member 16 having the light source therefor built therein and the assistant microscope 14 are attached, there is no possibility of said rotatable member 16 interfering with the operator's surgical operation. Since the assistant microscope 14 is adapted to have its objective lens 15 positioned between said operating microscope 10 and said rotatable member 16, the viewing angle a of the assistant microscope 14 relative to the cornea can be made sufficiently small. That is, whereas the objective lens 15 of the assistant microscope 14 was conventionally disposed at the position shown in phantom lines in FIG. 1 and hence the standard value of said viewing angle a' ranged from about 19 degrees to about 27 degrees, in the present invention said viewing angle a is reduced to about 8 degrees. Therefore, substantially the same field of vision as that for the operator can be attained by the assistant microscope 14.

In the above embodiment, the fluorescent lamp 21 and stroboscopic lamp 22 have been used as the light source; however, the light source is not limited thereto and LED, optical fiber, electric bulbs (tungsten and halogen), etc., may, of course, be used in single or in plurality. Further, in the above embodiment, the support shaft 27 for the microscope 10 has been supported in the bearing 25; however, any conventional means may, of course, be used provided that such means is capable of allowing the rotatable member 16 to rotate relative to the microscope 10 for selectively switching between the irradiating position on the optical axis and the retracted position.

EFFECTS OF THE INVENTION

As has so far been described, the rotatable member having a light source section is rotatably attached to the operating microscope such that said light source can be selectively switched between the irradiating position on the optical axis and the retracted position. Therefore, if the rotatable member found forming an obstacle during ophthalmic operation, it can be rotated through about 180 degrees, thereby widening the space above the cornea of the patient. Thus, there is no possibility of the rotatable member interfering with the operator's surgical operation, and an assistant microscope can be attached as such to said operating microscope. Further, when the assistant microscope is attached such that the position of the objective lens of the assistant microscope is located between the lower end surface of the operating microscope and the rotatable member, the viewing angle of the assistant microscope relative to the cornea of the patient can be made sufficiently small, whereby the accurate shape of the cornea can be observed all the time.

What is claimed is:

1. An auto-keratometer which is adapted to be attached to an operating microscope having an optical axis, a main body, an eyepiece in an upper region of said main body, and an objective lens in a lower region of said main body for measuring the corneal refraction or corneal astigmatic condition by detecting light from a light source reflected by a cornea through the intermediary of said objective lens and a beam splitter, said auto-keratometer comprising:
    (A) an annular light source unit having an axis and a circular slit formed in a horizontal plane for irradiation of light downwardly therethrough; and
    (B) means for holding said annular light source unit on said main body of said operating microscope in such a manner that said annular light source unit is movable in a horizontal plane between
        (i) an irradiation position at which the axis of said annular light source unit is aligned with the optical axis of said operating microscope, and
        (ii) a laterally retracted position at which said annular light source unit is removed from a workspace beneath said objective lens of said operating microscope.

2. An auto-keratometer as set forth in claim 1, wherein said means for holding said annular light source unit comprises an attaching table fixed to said main body of said operating microscope at a position laterally adjacent to said objective lens, said attaching table having a support shaft which extends vertically and downwardly from said attaching table, a connecting member pivotally carrying said annular light source unit at one end for rotation about said support shaft so that said annular light source unit is movable for rotation between the irradiation position at which said annular light source unit is located beneath said objective lens of said operating microscope, and the laterally retracted position.

3. A auto-keratometer as set forth in claim 2; and further comprising an assistant microscope attached to said main body of said operating microscope and having a line of sight, said assistant microscope having an assistant objective lens which is located near said objective lens of said operating microscope, said annular light source unit being positioned in the line of sight of said assistant objective lens of said assistant microscope when said annular light source unit is in the irradiation position.

4. An auto-keratometer as set forth in claim 3, wherein said assistant objective lens of said assistant microscope is located close to said objective lens of said operating microscope and opposite to said connecting member for holding said annular light source unit.

5. An auto-keratometer as set forth in claim 1, wherein said means for holding said annular light source unit includes means for selectively setting said annular light source unit at an upper limit position for measuring a corneal shape in a central narrow region of the cornea and at a lower limit position for measuring a corneal shape in a wider region of the cornea.

6. An auto-keratometer as set forth in claim 1, wherein said annular light source unit has a built-in first light source for illuminating the cornea and a built-in second light source for measuring the corneal shape.

7. An auto-keratometer as set forth in claim 6, wherein said first light source is a fluorescent lamp and said second light source is a stroboscopic lamp.

* * * * *